(12) United States Patent
Maiorano et al.

(10) Patent No.: US 10,071,173 B2
(45) Date of Patent: Sep. 11, 2018

(54) FIDUCIAL MARKER FOR USE IN STEREOTACTIC RADIOSURGERY AND PROCESS OF PRODUCTION

(71) Applicant: FONDAZIONE ISTITUTO ITALIANO DI TECNOLOGIA, Genoa (IT)

(72) Inventors: Gabriele Maiorano, S. Cesarea Terme (IT); Elisa Mele, Castrignano Dei Greci (IT); Athanasia Athanasiou, Ceranesi (IT); Pier Paolo Pompa, Lecce (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 0 days.

(21) Appl. No.: 15/564,786

(22) PCT Filed: Apr. 5, 2016

(86) PCT No.: PCT/IB2016/051914
§ 371 (c)(1),
(2) Date: Oct. 6, 2017

(87) PCT Pub. No.: WO2016/162784
PCT Pub. Date: Oct. 13, 2016

(65) Prior Publication Data
US 2018/0110884 A1    Apr. 26, 2018

(30) Foreign Application Priority Data

Apr. 7, 2015 (IT) .......................... 102015000011062

(51) Int. Cl.
*A61K 9/00* (2006.01)
*A61K 49/04* (2006.01)

(52) U.S. Cl.
CPC .................................. *A61K 49/04* (2013.01)

(58) Field of Classification Search
CPC ....................................................... A61K 49/04
See application file for complete search history.

(56) References Cited

U.S. PATENT DOCUMENTS

2008/0234532 A1* 9/2008 De Langen ............ A61B 90/39
600/8
2014/0343413 A1 11/2014 Jolck et al.

OTHER PUBLICATIONS

Meagher, M.J., et al., Dextran-encapsulated barium sulfate nanoparticles prepared for aqueous dispersion as an X-ray contrast agent. Journal of Nanoparticle Research, 2013. 15:2146, 10 pages.

(Continued)

*Primary Examiner* — Paul W Dickinson
(74) *Attorney, Agent, or Firm* — Thomas Horstemeyer, LLP

(57) ABSTRACT

Composition in the form of a shaped device, for use as a fiducial marker in tissues in the animal body, in radiotherapy and/or radiosurgery, characterized in that it comprises:—a core consisting of a colloidal dispersion of metal nanoparticles and/or oxides or metal salts having X-ray-contrast properties, where said nanoparticles are stabilized with surfactants, polymers or capping agents in a liquid vehicle, and—a polymeric casing that encapsulates the core, said device having a minimum size of not less than 500 microns and a maximum size not greater than 3000 microns.

9 Claims, 1 Drawing Sheet

(56) References Cited

OTHER PUBLICATIONS

Figure 1:
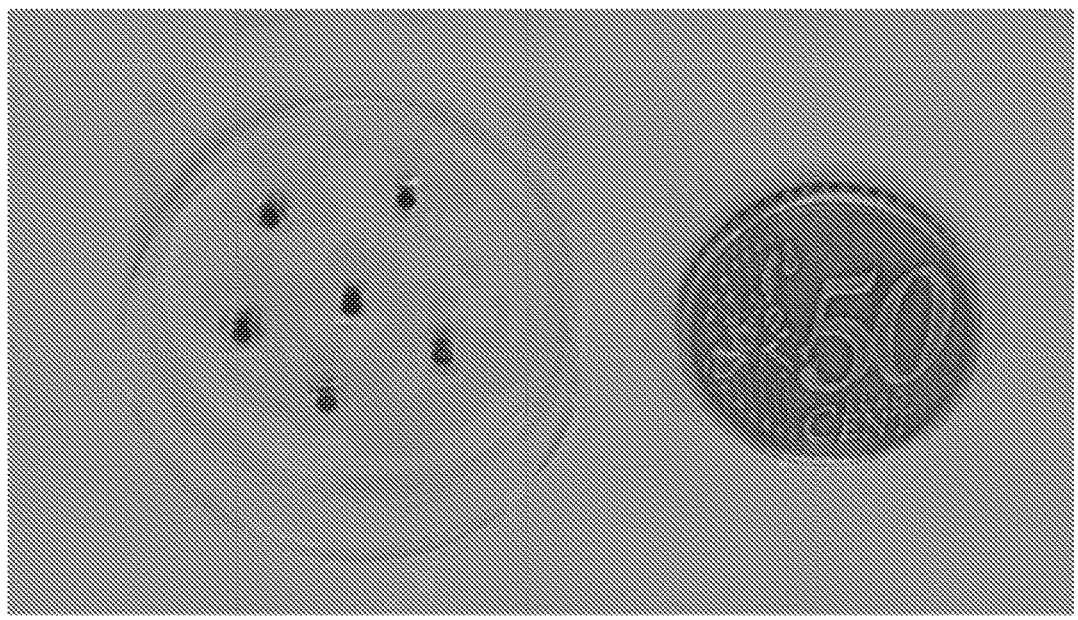

Jolck, R.I., et al., Injectable colloidal gold in a sucrose acetate isobutyrate gelating matrix with potential use in radiation therapy. Advanced Healthcare Materials, 2014. 3(10): p. 1680-7.

International Search Report for PCT/IB2016/051914 dated Jul. 1, 2016.

Xu, et al., "Real-time tumor tracking using implanted positron emissions markers: Concept and simulation study", Med. Phys. 33 (7), Jul. 2006, pp. 2598-2609.

Astolfo, et al., "A simple way to track single gold-loaded alginate microcapsules using x-ray CT in small animal longitudinal studies", Nanomedicine: Nanotechnology, Biology, and Medicine, 10 (2014) 1821-1828.

Badawi, et al., "Effect of Gold Nanoparticles Contrast Agent Concentration on X-Ray Diagnoses: Experimental and Computational Study", American Journal of Nanoscience and Nanotechnology, 2014; 2(4): 63-69.

* cited by examiner

FIDUCIAL MARKER FOR USE IN STEREOTACTIC RADIOSURGERY AND PROCESS OF PRODUCTION

CROSS-REFERENCE TO RELATED APPLICATION

This application is the 35 U.S.C. § 371 national stage application of PCT Application No. PCT/162016/051914, filed Apr. 5, 2016, where the PCT claims priority to and the benefit of, IT Patent Application No. 102015000011062, filed Apr. 7, 2015, both of which are herein incorporated by reference in their entireties.

The present invention relates to compositions of structured material for use as fiducial markers, particularly in modern stereotactic radiosurgery oncology, and to a process for the preparation thereof.

Radiotherapy, or the application of ionizing radiation capable of damaging the DNA of a target biological tissue, has proven to be a crucial treatment in modern oncology, alone or in combination with surgical treatment and/or systemic therapy. This evidence is corroborated by the percentage of oncology patients that are subjected to radiotherapy, namely 60%. Therefore, modern radiotherapy oncology is independent of often palliative solutions, reserved for situations that are non-surgical or with symptoms to be combatted, and is establishing itself as an increasingly primary therapeutic opportunity, an alternative if not a priority with respect to surgery, for various forms of tumour. New highly advanced technological equipment makes it possible in fact to strike the target tumour very precisely, while sparing the nearby tissues from irradiation. On the contrary, conventional radiotherapy techniques may cause serious damage also to the tissues surrounding the neoplasia, rendering them very burdensome to the patient, and sometimes cannot be carried out for the purpose of eradication. The technological advent which has revolutionized this therapeutic approach was the introduction of intensity modulated radiotherapy (IMRT) and image guided radiotherapy (IGRT).

In the IMRT technique, incident radiation beams of non-uniform intensity are directed on the patient in such a way as to model the distribution of the radiation dose to the volumes of interest. The personalization of the dose distribution to the volumes of interest takes place using multileaf collimators (binary or conventional), passive modulators or dedicated accelerators, only after the development of appropriate planning techniques of an inverse or forward nature (as for the latter less pursued). Currently, various technological and/or commercial solutions on the principle of IMRT are employed: classical IMRT, VMAT (Volumetric Modulated Arc Therapy), Rapid Arc®, tomotherapy and Cyberknife®. The IMRT techniques allow irradiation with absolute precision and with higher radiation doses and also target volumes of complex shape and/or localized in close proximity to adjacent organs which are not able to tolerate the doses required to control the neoplasia. However, the presence of strong dose gradients and the use of non-uniform incident beams, especially if generated in dynamic mode, render the treatment particularly susceptible to errors and uncertainties in the changes of position during the irradiation due to imprecise positioning of the patient and/or to the movements which the tumour mass can demonstrate (due to physiological actions such as breathing, peristalsis, arterial pulsations for example). To overcome these limitations, together with the development of IMRT, IGRT was introduced. This technique makes use of the new diagnostic imaging technologies such as magnetic resonance imaging (MRI), positron emission tomography (PET), cone beam or conical beam computed tomography (CBCT) which reveal, prior to each treatment, the current position of the patient, of the target tumour and of the internal critical organs. By means of continuous comparison with the images taken in the radiotherapeutic planning phase, repositioning errors are corrected in real time and the radiation energy is adjusted at the precise target. The instruments designed for this purpose in practice allow the performance of the radiotherapeutic treatment to be controlled in real time, localizing the tumour and correcting the modes of delivery of the irradiating beam, in order to reproduce the treatment plan to within a millimeter in relation to potential morphological changes in the target (adaptive radiotherapy, ART). The technological revolution brought about by the IMRT-IGRT techniques has introduced the concept of radiosurgery, used to direct three-dimensional stereotactic irradiation on a target using external beams, accompanied by a computerized system of planning of the appropriate three-dimensional treatment. Various factors characterize and differentiate the radiosurgical technique from the radiotherapeutic technique: in fact the ablative purpose of the former requires the use of high doses of radiation in a single session of treatment or in a few sessions (2-5 fractions), whereas in radiotherapy a high number of sessions are conducted: even 30-40 fractions may be necessary depending on the type of pathology.

The most advanced evolution of radiosurgery is represented by CyberKnife®, a robotized stereotactic radiosurgery system, devised in 1997 by the United States neurosurgeon John R. Adler (Stanford University) and by Peter and Russell Schonberg (Schonberg Research Corporation) and developed by the Accuray company. This takes the form of a compact linear accelerator mounted on a computer-guided robotic arm with six degrees of freedom. Its functioning is based on the irradiation (performed by high energy X-rays) of the patient from different angles. The radiotherapy is optimized by virtue of continuous monitoring of the position of the tumour using a synchronized system of stereoscopic X-rays and LEDs applied to the thorax of the patient. The thoracic LEDs allow the tumour to be tracked while the patient is breathing and to automatically interrupt the administration in case of abrupt movement. The X-ray monitoring, on the other hand, serves to locate the tumour, to keep it monitored, to correct the LED-breathing calibration and to locate the non-target tissues in order to implement a therapeutic planning. These measures allow a total clinical accuracy of less than 0.95 mm for fixed lesions.

In radiosurgery, the localization of the tumour is carried out by means of comparing images based on reference points on the skull for intracranial lesions and on the vertebral column for spinal lesions. For lesions of soft tissues on the other hand, the implantation of fiducial markers is required, consisting of fragments of radio-opaque material, mainly gold, usually cylindrical, varying from 1 to 5 mm in size, and inserted near the tumoral lesion in numbers ranging between 3 and 8. The insertion of the markers is carried out in an operative phase by means of ultrasound-guided injection. In fact, soft tissues, being radiotransparent, do not allow the use of any (radio-opaque) bone structure as a point of reference. In this manner, the images in vivo based on the fiducial markers are the basis of the manipulator control; these are compared in fact with the computed tomography which was employed for the planning of the treatment. The fiducial markers, therefore, by creating an internal system coordinates which permits an accurate visualization of the anatomical area of interest and a precise alignment with that of the treatment beams, afford the most direct solution to the requirements of correct positioning and repositioning of the patient exactly for the stereotactic surgery, in terms both of verifying the setup prior to the treatment and of tracking the organ motion between fractions.

The positioning of fiducial markers is now a tried-and-tested technique for neoplastic prostatic lesions, whereas the clinical validation for neoplastic lesions of the lungs, liver, pancreas, neck and paraspinal lesions is still in progress. The use of solid fiducial markers provides an excellent radiological contrast but the insertion into the tumour or its surroundings is an invasive procedure owing to the considerable size of the solid implant, which therefore requires adequately sized and specialized needles for the implant. Numerous side effects follow the positioning of the fiducial markers, especially in patients affected by pulmonary neoplasias (pneumothorax reported in 33-68% of patients), inflammation, haemorrhage, migration of the markers and infections. The side effects and the insertion procedure of the fiducial markers create some limitations regarding the use of this technological solution in all soft tissues potentially treatable by means of stereotactic radiosurgery. Further limitation is seen in patients with specific clinical situations that predispose to a higher incidence of side effects. Therefore, there is continuous research and development of new technological solutions which can reduce side effects and expand the fields of application with respect to target tissues of major oncological relevance, such as the liver, lung and pancreas.

Recent studies report evidence of higher contrasting power from nanostructured material relative to the same material macrostructured (bulk); this characteristic has been observed both in nanoparticles of barium sulphate and in nanoparticles of gold. Therefore, the development of fiducial markers based on nanomaterials would allow the reduction of the sizes of the system and the costs, guaranteeing at the same time the typical contrast efficiency of non-nanostructured material of greater size. The overall reduction in the size of the fiducial marker would bring great advantages in terms of easier, and therefore more effective and less risky, positioning within a greater number of target tissues (by endoscopy for example).

The strategies adopted to date for the development of fiducial markers based on nanoparticulate systems have made use of microcapsules and/or composites prepared by gelification and containing nanoparticles of gold [2-4] and nanoparticles of barium sulphate encapsulated by dextran through microemulsion [5]. Such systems suffer from some important technical limitations such as:
1. The nanomaterial is incorporated in a matrix which acts as solidifier and in this way the nanoparticle solution is diluted, thus causing a significant decrease in the contrasting power, which is proportional to the concentration of the nanomaterial in the volume of the fiducial marker [1].
2. No adequate chemical isolation of the nanoparticulate system which therefore leads to a direct interaction with the biological tissue in which it is located. The interaction of the nanomaterial with biological fluids involves interactive phenomena which are capable of modifying the colloidal stability of the system and thus the contrast efficacy. Disintegration and dissolution phenomena of the matrix may also occur, with consequent loss of efficacy of the fiducial marker and possible adverse biological effects. These disadvantages have been reported by Jølck and colleagues [2]: in their study a release of nanoparticles of gold from the nanogel is observed which they seek to limit by increasing an additive within the formulation. In the same study, a modification of the colloidal system once implanted in vivo is also reported, a modification which leads to the nanoparticles accumulating at the interface of the margin of the nanogel.
3. Poor control of the morphology of the capsule which cannot be modelled for optimal insertion by endoscopic methods and to prevent the effects of spontaneous migration.

SUMMARY OF THE INVENTION

For the purpose of overcoming the disadvantages mentioned above, the present invention relates to structures comprising a core of a colloidal dispersion of nanoparticles in a solid casing which envelops said core, having millimetric or micrometic dimensions, to be used as fiducial markers, in particular in modern stereotactic radiosurgery oncology and a procedure for the preparation thereof as defined in the attached claims.

The colloidal dispersion is composed of radio-opaque nanoparticles.

The external coating is composed of a biocompatible polymer which provides for a chemical and physical isolation of the colloidal dispersion and gives the product thus manufactured sufficient properties of elasticity, flexibility and robustness. The polymer (and thus the final form of the capsule) may be sized and modelled and/or micro/nano-structured and/or chemically modified such that the fiducial marker possesses the characteristics suitable for insertion in the target tissue even by non-invasive techniques such as endoscopy and so that involuntary migration of the fiducial marker is minimized if not completely absent.

DETAILED DESCRIPTION OF THE INVENTION

The invention relates to fiducial markers comprising a highly concentrated and physicochemically stable colloidal dispersion of nanoparticles, coated externally by a biocompatible polymer which gives the product characteristics of robustness, flexibility and elasticity.

In detail, the nanoparticulate solution is composed of a dispersion of metallic nanoparticles and/or metal oxides and/or metal salts whose respective bulk materials already have evidence of good contrast properties in a liquid vehicle.

The nanoparticles are generally solid particles visible at least by means of visualization by computed tomography (CT).

Therefore, they consist of or comprise X-ray contrast agents which include transition metals, rare earth metals and alkali metals or alkaline earth metals.

For example, the material of such X-ray contrast agents may be selected from gold, bismuth, gadolinium, iron, barium, calcium and magnesium; particularly preferred are particles of metallic gold which constitutes the material currently used for standard fiducial markers for CyberKnife® radiosurgery, although in this case in cylindrical form of sizes from 1 to 5 mm.

However, the material for the nanoparticles should not be understood as being limited to the materials cited above in as far as it should not be understood as excluding the use of particles comprising radioactive or paramagnetic compounds, selected depending on the mode of visualization used.

The sizes of the nanoparticles are from 1 nanometer to 1000 nanometers, preferably between 50 and 200 nanometers.

The concentration of nanoparticles in the vehicle is typically greater than 1 mg/mL, preferably greater than 50 mg/mL.

The nanoparticles in solution are stabilized by surfactants and/or polymers and/or capping agents, for example:

polyethylene glycol CAS 25322-68-3, and derivatives of polyethylene glycol, monofunctionalized (for example methoxypolyethylene glycol amine CAS 80506-64-5, polyethylene glycol 2-mercaptoethyl methyl ether CAS 134874-49-0) and bifunctionalized (homo-bifunctionalized such as, for example, polyethylene glycol diamine CAS 24991-53-5, and hetero-bifunctionalized such as, for example, polyethylene glycol 2-mercaptoethyl ether acetic acid CAS 165729-81-7);
polyvinylpyrrolidone CAS 9003-39-8;
hexadecyltrimethylammonium bromide CAS 57-09-0;
hexadecyltrimethylammonium chloride CAS 112-02-7;
sodium dodecyl sulphate CAS 151-21-3;
dodecyltrimethylammonium bromide CAS 1119-94-4;
dodecyltrimethylammonium chloride CAS 112-00-5;
polyvinyl alcohol CAS 9002-89-5;
n-dodecyl mercaptan CAS 112-55-0;
bovine serum albumin CAS 9048-46-8;
tannic acid CAS 1401-55-4;
4-(2-hydroxyethyl)-1-piperazinylethanesulphonic acid (HEPES) CAS 7365-45-9;
piperazine-N,N'-bis(2-ethanesulphonic acid) (PIPES) CAS 5625-37-6;
3-(N-morpholino)propanesulphonic acid (MOPS) CAS 1132-61-2;
2-(N-morpholino)ethanesulphonic acid (MES) CAS 4432-31-9;
—N-cyclohexyl-2-aminoethanesulphonic acid (CHES) CAS 103-47-9;
—N-cyclohexyl-2-aminopropanesulphonic acid (CAPS) 1135-40-6;
3-[4-(2-hydroxyethyl)-1-piperazinyl]propanesulphonic acid (HEPPS) CAS 16052-06-5;
sodium citrate CAS 6132-04-3;
boric acid and salts thereof preferably compounds of natural origin, preferably negatively charged compounds, preferably compounds used in a biological context and recognized as safe.

The nanomaterial is dispersed in an aqueous solution or in one of the compounds below, such as, for example:
glycerol CAS 56-81-5;
dimethyl sulphoxide CAS 67-68-5;
dimethylformamide CAS 68-12-2;
ethylene glycol CAS 107-21-1;

preferably hydrophilic compounds, preferably compounds used in a biological context and recognized as safe.

The polymer which coats the solution of nanoparticles is composed of natural and/or synthetic and/or bio-inspired precursors to which adjuvant compounds of natural and/or synthetic origin may optionally be added, for example:
poly(tetrafluoroethene) CAS 9002-84-0;
poly(dimethylsiloxane) CAS 63148-62-9;
poly(propene) CAS 9003-07-0;
polyethylene terephthalate CAS 25038-59-9;
aliphatic and semi-aromatic polyamides: example Nylon 6-6 CAS 32131-17-2;
aromatic polyamides (aramids): examples Kevlar® and Nomex®;
thermoplastic polyurethanes: example Pellethane®;
poly(ether urethane ureas): example Biomer®;
low or high density polyethylenes CAS 9002-88-4;
polysulphones;
polyvinyl chloride CAS 9002-86-2;
poly(2-hydroxyethyl methacrylate) CAS 25249-16-5;
poly(methyl 2-methylpropenoate) CAS 9011-14-7;
polyesters;
polysiloxanes: example MED-4750® NuSil Technology;
hydrogel;
other acrylic polymers;

preferably polymers based on silicone elastomers and/or polydimethylsiloxane.

Drugs and/or natural and/or synthetic compounds can be added to the polymers for controlled release of such substances in the organ in which the marker is implanted.

The fiducial markers that are the object of the invention preferably have a size of 500 to 3000 µm; particularly in the case of non-spherical structures, characterized by two principal dimensions, such as the gold cylinders currently used, a minimum size preferably not less than 500 µm and a maximum size not more than 2000 µm.

They may be prepared by the following general procedures:

moulding of a solution of the polymer, preferably silicone-based, added to its curing agent, in a mould of specific shape and texture. To this solution is added, by means of a capillary, a drop of known volume (from 0.01 to 100 microliters, preferably 1-3 microliters) of a solution of nanoparticles prepared according to the procedures described above. The liquid vehicle of the nanoparticle solution may be selected to obtain a difference in the value of the surface tension between polymer and vehicle such that the drop containing the nanomaterial remains stable without any solubilization phenomenon within the polymeric matrix. The polymer with the nanoparticle solution within is subjected therefore to a polymerization process at temperatures not exceeding 100° C., preferably at 60° C., in a period not exceeding 24 hours, in order to contribute further to preserving the colloidal stability of the nanoparticles present within;

alternatively, the fiducial marker that is the object of the invention may also be achieved by producing a hollow object of polymeric material. The cavity is sized so as to accommodate a specific volume of nanoparticulate solution which is injected through the polymeric matrix. The insertion of the nanomaterial solution into the cavity is carried out using adequately sized capillaries. The points of insertion and withdrawal of the capillaries in the polymer are subsequently sealed by means of a controlled polymerization of the holes by addition of polymeric precursor and curing agent and/or an additional heating cycle. The hollow object can be fashioned in the following ways:

1. moulding of a precursor solution of the polymer in a mould of specific shape and texture. By means of a capillary, a drop of known volume (from 0.01 to 100 microliters) of water and/or glycerol and/or dimethyl sulphoxide and/or dimethylformamide and/or ethylene glycol is added within the polymeric solution. By the appropriate values of surface tension determined by precise use of the particular polymer and the particular solution, the drop deposited within the polymeric solution remains stable. The polymer with the drop within is subjected therefore to a process of controlled polymerization. Subsequently, through the insertion of two adequately sized capillaries (inlet and outlet), the solution of the drop contained within the object is replaced with the solution of nanoparticles previously prepared as described.

2. Creating an object with a known cavity volume by three-dimensional moulding of the polymer of interest.

Subsequently, through the insertion of two adequately sized capillaries (inlet and outlet), the solution of the drop contained within the object is replaced with the solution of nanoparticles previously prepared as described.

The technological solution that is the object of the present invention provides for the encapsulation of nanoparticle solutions of high contrasting power within a biocompatible polymer which guarantees chemical and physical protection of the nanoparticle solution from the biological surroundings in which the fiducial markers are implanated and vice versa. The creation of such a system provides for the modulation of two important aspects constituting the object: the colloidal dispersion and the coating polymer.

Regarding the colloidal dispersion of nanoparticles, it is required first of all to preserve the stability of the nanoparticulate system from the synthesis up to the final phases of preparation of the fiducial marker. Operating with this knowledge, aggregation and/or agglomeration phenomena, which would lead to the material microstructuring, thus losing to a large extent the contrast efficiency, are avoided. Setting this technical objective as the cornerstone, it is preferable to meet also one or more of the requirements reported below:
1. achieve high concentrations of nanomaterials since the concentration of nanoparticles is proportional to the concentration of the nanomaterial in the volume of the fiducial marker [1];
2. coat the nanoparticles with a compound that stabilizes them electrostatically and is a good neutral or basic buffer (pKa>6) so as to protect the colloids from secondary products of polymerization of the coating polymer;
3. disperse the nanoparticles in a liquid phase with a surface tension value greater than 65 dyn/cm so as to be able to be inserted in the polymeric matrix without dispersion phenomena of the drop;
4. disperse the particles in a liquid phase having characteristics in terms of density and viscosity so as to counter the natural tendency of the nanomaterial towards sedimentation over time;
5. disperse the nanoparticles in a liquid phase having a high boiling temperature in order to preserve the nanomaterial from the increase in temperature necessary for the polymerization of the external coating.

The preparation of gold nanoparticles of diameter from 5 to 200 nm, preferably of 100 nm, coated with 4-2-hydroxy-ethyl-1-piperazinylethanesulphonic acid at a concentration of 50 to 800 mg/ml, preferably of 300 mg/ml, dispersed in glycerol, is the ideal technical solution to meet all the necessary characteristics. In fact, such a preparation preserves unaltered the plasmonic peak centred at the maximum wavelength of 565 nm, indicating an excellent colloidal stability during the whole process of preparation of the marker.

Regarding the polymer which constitutes a preferably continuous (non-fibrous) coating, silicone elastomers possess the desirable characteristics for manufacturing the fiducial markers that are the object of the invention. The polymerization procedure may not ignore the fundamental requirement set out above, namely the protection of the colloidal stability of the nanoparticulate system, the guarantee of contrast efficiency. Therefore, the proportions of polymeric precursor/curing agent and/or polymerization temperature and/or polymerization time must be accurately calibrated on this basis. The use of Sylgard 184® or MED-4750® NuSil Technology, in combination with AuNPs coated with 4-2-hydroxyethyl-1-piperazinylethanesulphonic acid dispersed in glycerol, is the ideal experimental strategy able to meet all the necessary requirements.

TABLE 1 differences in contrasting power between standard fiducial markers present on the market and the fiducial markers of the invention.

|  | Hounsfield number (measured in phantom tissue equivalents) |
| --- | --- |
| Standard fiducial marker | 2000-5000 |
| Inventive fiducial marker | 7000 |

Figure 2:
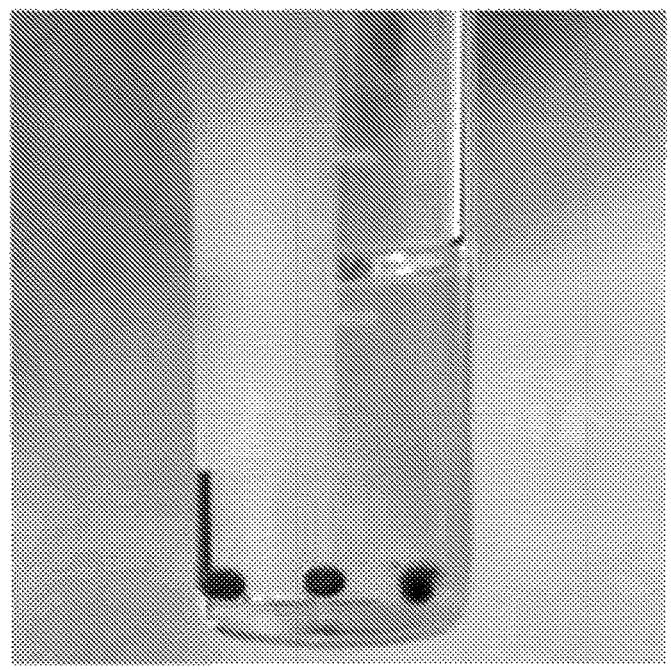

In the attached drawings:
FIG. 1 is a photograph that illustrates fiducial markers that are the object of the invention consisting of a colloidal dispersion of AuNPs coated with silicone polymer obtained according to example 2 below;
FIG. 2 is a photograph that illustrates fiducial markers that are the object of the invention suspended in silicone-based liquid phase (Alfasil®).

EXAMPLE 1: PREPARATION OF THE COLLOIDAL SOLUTION OF NANOPARTICLES

In a typical example of manufacture, the preparation procedure of the solution of nanoparticles, in this case of gold (AuNPs), is carried out as follows: AuNPs of approximately 100 nm are synthesized by means of seed-mediated growth (using as seeds particles of gold of 15 nm, capped with citrate, synthesized by procedures of the Turkevich-Frens type). After the synthesis, the particles are stabilized by adding an appropriate amount of 4-2-hydroxyethyl-1-piperazinylethanesulphonic acid (HEPES) (from 1 to 5000 micromolar for example), and are then concentrated by means of repeated centrifugation and redispersal in glycerol until a concentration preferably >50 mg/ml is reached, in this case 300 mg/ml. Such solutions are stable for months even under ambient conditions, and are thus used for encapsulation in the polymer by the general procedure reported below.

EXAMPLE 2: PREPARATION OF THE MARKER

In a typical preparation example, the silicone elastomer Sylgard 184® is used mixed in a 10:1 proportion with the corresponding curing agent. Into the solution thus prepared, a volume of nanoparticulate dispersion prepared as described is added. This is therefore heated so that the decomposing organic peroxides can result in the ethylenic bridge between the polymeric chains. The polymerization temperature does not exceed 60° C. in order not to alter the nanoparticulate solution contained within the fiducial marker that is the object of the study. In an alternative, which is moreover preferred, the silicone elastomer MED-4750® NuSil Technology may be used, the polymerization being carried out according to standard procedures (at ambient temperature for example).

Fiducial markers of spheroidal shape (of 2 mm diameter for example) were produced using the polymers cited above using the moulding procedure in the mould previously described. The colloidal gold solution obtained according to example 1 in glycerol vehicle was introduced into the silicone polymer solution in the mould in an amount of 2 µl. The polymerization, as indicated above, was conducted at a temperature of 60° C. for a period of 2 hours.

These innovative fiducial markers are able to generate high intensity X-rays (Hounsfield number equal to 7000 compared to values for standard fiducial markers equal to 3000-5000). The use of nanoparticles makes it possible to obtain a high contrast with lower doses relative to corresponding non-nanostructured material, this advantage being apparent in the extremely reduced size of these objects (less than 3 mm) which makes them particularly applicable to be inserted in the patient endoscopically, allowing areas of the body to be reached, therefore, currently unexplored by radiosurgery. The fiducial markers that are the object of the invention possess many distinctive characteristics relative to injectable compositions of nanoparticles of contrast agents in gel-forming materials intended for systemic administration. Furthermore, the coating polymer used presents an excellent combination of properties of flexibility, elasticity and robustness and may be readily modelled and/or micro/nano-structured and/or chemically modified such that the fiducial marker may be inserted even more easily in the target tissue endoscopically and so that involuntary migration of the fiducial marker is minimized if not completely absent. Furthermore, the physical and chemical isolation offered by the polymer allows a durable colloidal stability of the nanoparticulate solution and thus a prolonged contrast efficiency. Another advantage offered by the external polymer consists of the biocompatability which makes it ideal as a long-lasting implantable medical device. Drugs and/or natural and/or synthetic compounds may also be added to the polymer for controlled release of such substances in the organ in which the marker is implanted. Furthermore, the particular technology allows extremely stable devices to be produced with a significantly lower overall cost than that of a single gold fiducial marker currently present on the market.

The marker thus assembled may be subjected to variations in size and/or micro/nanostructuring of the surface and/or surface chemistry, if desired, to facilitate the positioning using endoscopic techniques and/or to modulate the spontaneous migration of the implanted fiducial markers. This result may easily be obtained by means of appropriate moulding processes or 3D printing and/or post-production processes such as: cutting procedures (by blade or laser) and/or mechanical abrasion and/or chemical abrasion.

The object thus produced may be subjected to processes of chemical functionalization of its external surface to evaluate the modulation of a possible spontaneous migration of the implanted fiducial markers.

Drugs and/or natural compounds may be added to the polymer which encases the colloidal solution for controlled release of such substances in the organ in which the marker is implanted, so that the possibility can be evaluated of conferring also a drug-carrier function to the fiducial marker.

The possibility of also inserting in such capsules magnetic nanoparticles with high contrast under magnetic resonance opens up possible applications for fiducial markers based on MRI diagnostic imaging. By virtue of the extremely high concentrations of the AuNPs, the capsules so produced provide high contrast in X-ray imaging, finding application as fiducial markers to be employed in applications of Stereotactic Radiosurgery (SRS) and in particular as markers for radiosurgical treatment using CyberKnife® instrumentation.

BIBLIOGRAPHY

1. Badawi, M. I., et al., *Effect of Gold Nanoparticles Contrast Agent Concentration on X-Ray Diagnoses: Experimental and Computational Study*. American Journal of Nano Research and Application, 2014. 2(4): p. 63-69.
2. Jolck, R. I., et al., *Injectable colloidal gold in a sucrose acetate isobutyrate gelating matrix with potential use in radiation therapy*. Adv Healthc Mater, 2014. 3(10): p. 1680-7.
3. Astolfo, A., et al., *A simple way to track single gold-loaded alginate microcapsules using x-ray CT in small animal longitudinal studies*. Nanomedicine, 2014. 10(8): p. 1821-8.
4. US2014/0343413.
5. Meagher, M. J., et al., *Dextran-encapsulated barium sulfate nanoparticles prepared for aqueous dispersion as an X-ray contrast agent*. Journal of Nanoparticle Research, 2013. 15(12).

The invention claimed is:

1. A composition in the form of a shaped device, for use as a fiducial marker in tissues in an animal body, in radiotherapy and/or radiosurgery, comprising:
    a core consisting of a colloidal dispersion of components selected from the group consisting of metal nanoparticles, metal oxides, and metal salts having X-ray-contrast properties, where said components are stabilized with surfactants, polymers or capping agents in a liquid vehicle, and
    a polymeric casing that encapsulates the core,
    said shaped device having a minimum size of not less than 500 microns and a maximum size not greater than 3000 microns, wherein said polymeric casing comprises an encapsulating polymeric material selected from silicone elastomers, polydimethylsiloxane, or a combination thereof.

2. The composition according to claim 1, wherein one component is he nanoparticles, wherein said nanoparticles include colloidal gold with size from 50 to 200 nm.

3. The composition according to claim 1, wherein said nanoparticles are coated with 4-2-hydroxyethyl-1-piperazinylethanesulphonic acid.

4. The composition according to claim 1, wherein said liquid vehicle is selected from the group consisting of water, glycerol, dimethyl sulphoxide, dimethylformamide and ethylene glycol or their aqueous solutions.

5. The composition according to claim 1, wherein said liquid vehicle is glycerol.

6. The composition according to claim 1, wherein said colloidal dispersion comprises said nanoparticles at a concentration from 50 to 800 mg/ml in the liquid vehicle.

7. A method of stereotactic radiosurgery carried out on body tissues comprising:
    providing a composition and
    implanting said composition in said body tissue as a fiducial marker,
    wherein the composition is in the form of a shaped device, for use as a fiducial marker in tissues in an animal body, in radiotherapy and/or radiosurgery, comprising:
        a core consisting of a colloidal dispersion of components selected from the group consisting of metal nanoparticles, metal oxides, and metal salts having X-ray-contrast properties, where said components are stabilized with surfactants, polymers or capping agents in a liquid vehicle, and
        a polymeric casing that encapsulates the core,
        said shaped device having a minimum size of not less than 500 microns and a maximum size not greater than 3000 microns, wherein said polymeric casing comprises an encapsulating polymeric material selected from silicone elastomers, polydimethylsiloxane, or a combination thereof.

8. A process for production of a composition in the form of a shaped device, for use as a fiducial marker in tissues in an animal body, in radiotherapy and/or radiosurgery, comprising:
   a core consisting of a colloidal dispersion of components selected from the group consisting of metal nanoparticles, metal oxides, and metal salts having X-ray-contrast properties, where said components are stabilized with surfactants, polymers or capping agents in a liquid vehicle, and
   a polymeric casing that encapsulates the core,
   said shaped device having a minimum size of not less than 500 microns and a maximum size not greater than 3000 microns, wherein said polymeric casing comprises an encapsulating polymeric material selected from silicone elastomers, polydimethylsiloxane, or a combination thereof,
   wherein the colloidal dispersion of components comprises a dispersion of nanoparticles, and
   wherein said composition is shaped by moulding of a solution of the encapsulating polymeric material, introducing said dispersion of nanoparticles in volume from 0.01 to 100 μl into said moulded solution and polymerizing said encapsulating polymeric material in a mould.

9. A process for production of a composition comprising the steps of:
   moulding of a hollow polymeric body of an encapsulating polymeric material,
   introduction into a cavity of said hollow polymeric body of a vehicle selected from water, glycerol, dimethyl sulphoxide, dimethylformamide or ethylene glycol or their aqueous solutions,
   polymerization of the encapsulating polymeric material, and
   insertion of a colloidal dispersion of nanoparticles in a liquid vehicle so as to replace the vehicle previously introduced in said cavity,
   wherein the composition is in the form of a shaped device, for use as a fiducial marker in tissues in an animal body, in radiotherapy and/or radiosurgery, the composition comprising:
      a core consisting of a colloidal dispersion of components selected from the group consisting of metal nanoparticles, metal oxides, and metal salts having X-ray-contrast properties, where said components are stabilized with surfactants, polymers or capping agents in the liquid vehicle, and
      a polymeric casing that encapsulates the core,
      said shaped device having a minimum size of not less than 500 microns and a maximum size not greater than 3000 microns, wherein said polymeric casing comprises the encapsulating polymeric material selected from silicone elastomers, polydimethylsiloxane, or a combination thereof.

* * * * *